United States Patent
Ronn et al.

(10) Patent No.: US 6,648,864 B2
(45) Date of Patent: Nov. 18, 2003

(54) ARRAY OF DISPOSABLE ABSORBENT ARTICLE CONFIGURATIONS AND MERCHANDISE DISPLAY SYSTEM FOR IDENTIFYING DISPOSABLE ABSORBENT ARTICLE CONFIGURATIONS FOR WEARERS

(75) Inventors: Karl P. Ronn, Cincinnati, OH (US); Barry R. Feist, Cincinnati, OH (US); Mary L. Carr, Cincinnati, OH (US); Kathy Q. Ames-Ooten, Cincinnati, OH (US); Danielia T. Wilkins, Cincinnati, OH (US); Merlene A. Cummins, Taylor Mill, KY (US); Ooma B. Rampersad-Cutler, Mason, OH (US); Monica J. Mohlenkamp, Cincinnati, OH (US); Vicki L. Streithorst, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 33 days.

(21) Appl. No.: 09/735,258

(22) Filed: Dec. 12, 2000

(65) Prior Publication Data

US 2002/0072723 A1 Jun. 13, 2002

(51) Int. Cl.[7] .................................. A61F 13/15
(52) U.S. Cl. .................................. 604/385.01; 604/358
(58) Field of Search .................................. 604/317–402; 2/267, 268, 400–408, 244

(56) References Cited

PUBLICATIONS

Copy of Box of "Tampax multipax", 1999.*
Advertisements: "Introducing Pampers Phases", Sep. 1991.
"Introducing New! Luvs Phases", Jan. 1992.
"Introducing! The First Specially Designed Diaper Made Just For Your Walker", Sep. 1991.
"Dial–A–Wheel", Sep. 1991.

* cited by examiner

Primary Examiner—Jeanette Chapman
(74) Attorney, Agent, or Firm—Jay A. Krebs; Ken K. Patel

(57) ABSTRACT

An array of disposable absorbent article configurations is provided comprising a sequence of designs corresponding to a wearer's stages of development. A merchandising system facilitates consumers' selection of an absorbent article configuration by appropriately matching an absorbent article configuration with a particular wearer's stage of development. The system includes indicia exhibiting pictorial representations of the absorbent article configurations fitted to wearer's at corresponding stages of development enabling a consumer to choose the appropriate absorbent article configuration for a particular wearer

4 Claims, 9 Drawing Sheets

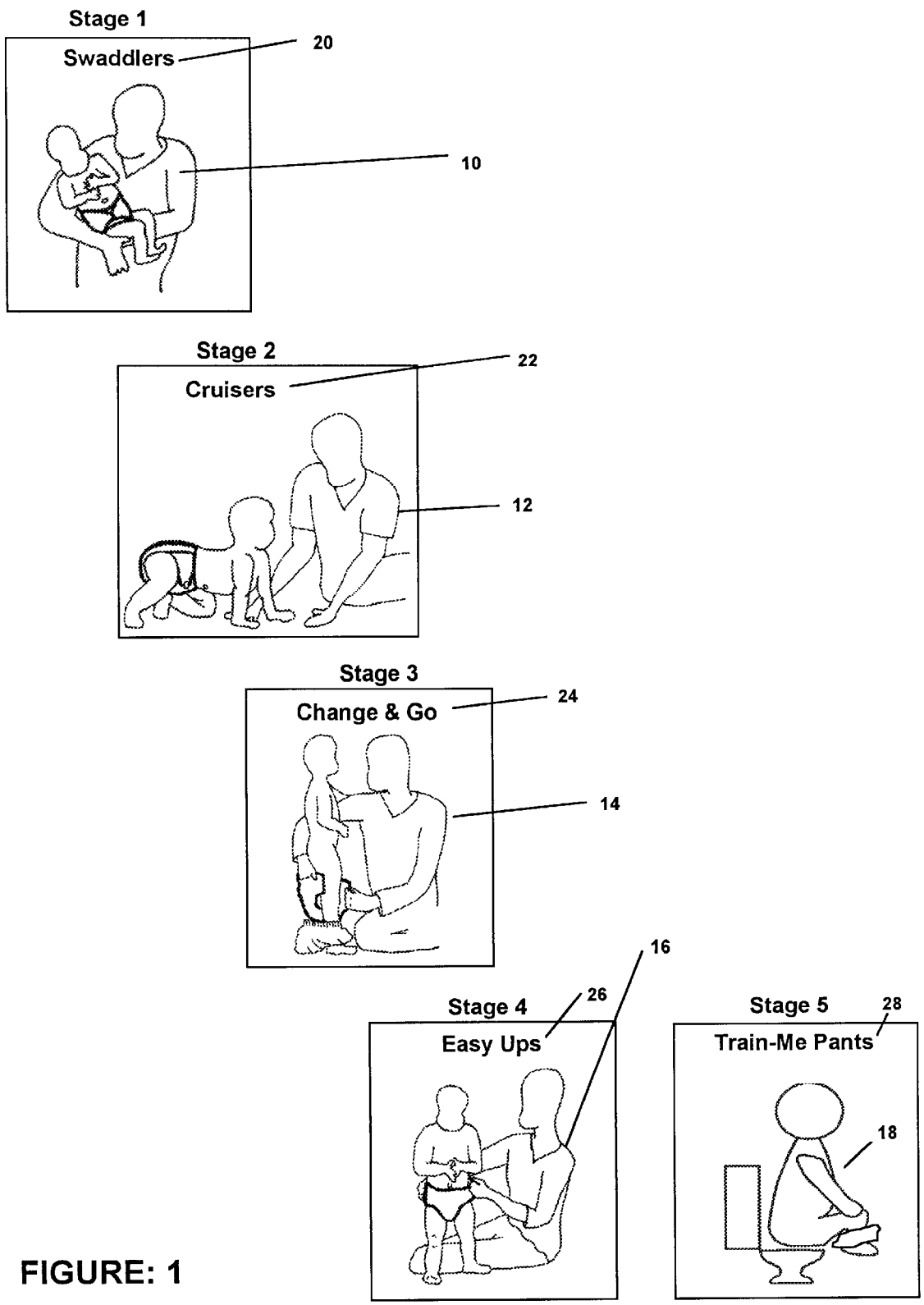
FIGURE: 1

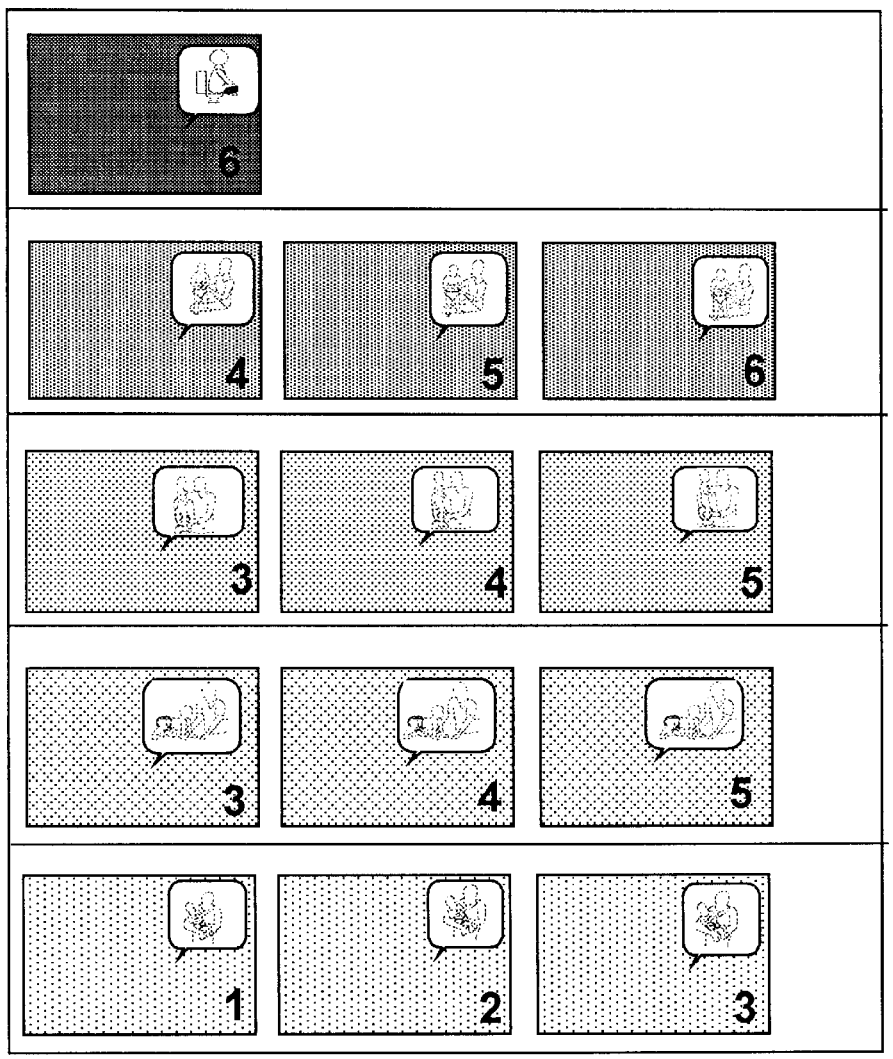
FIGURE: 2a

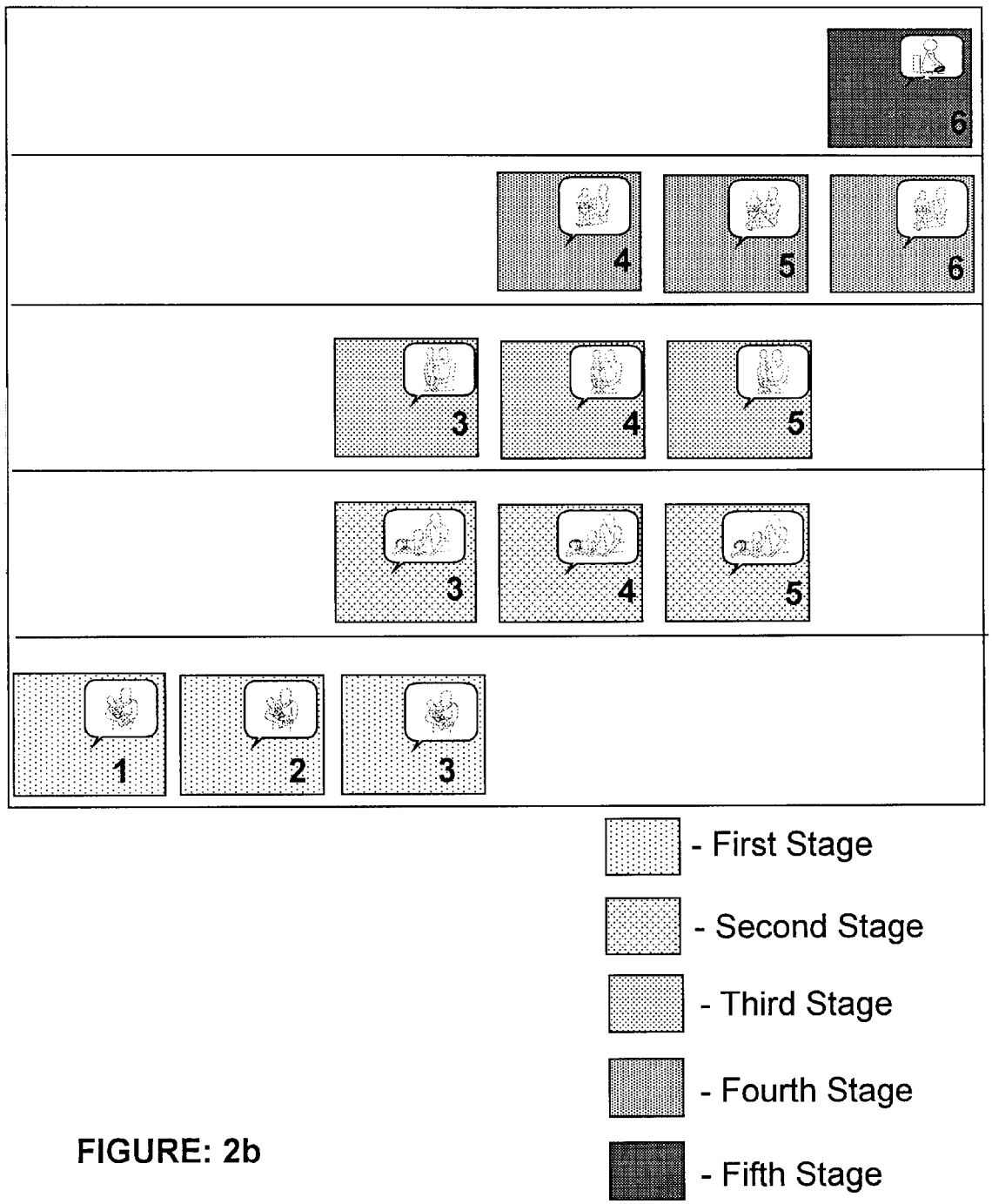
FIGURE: 2b

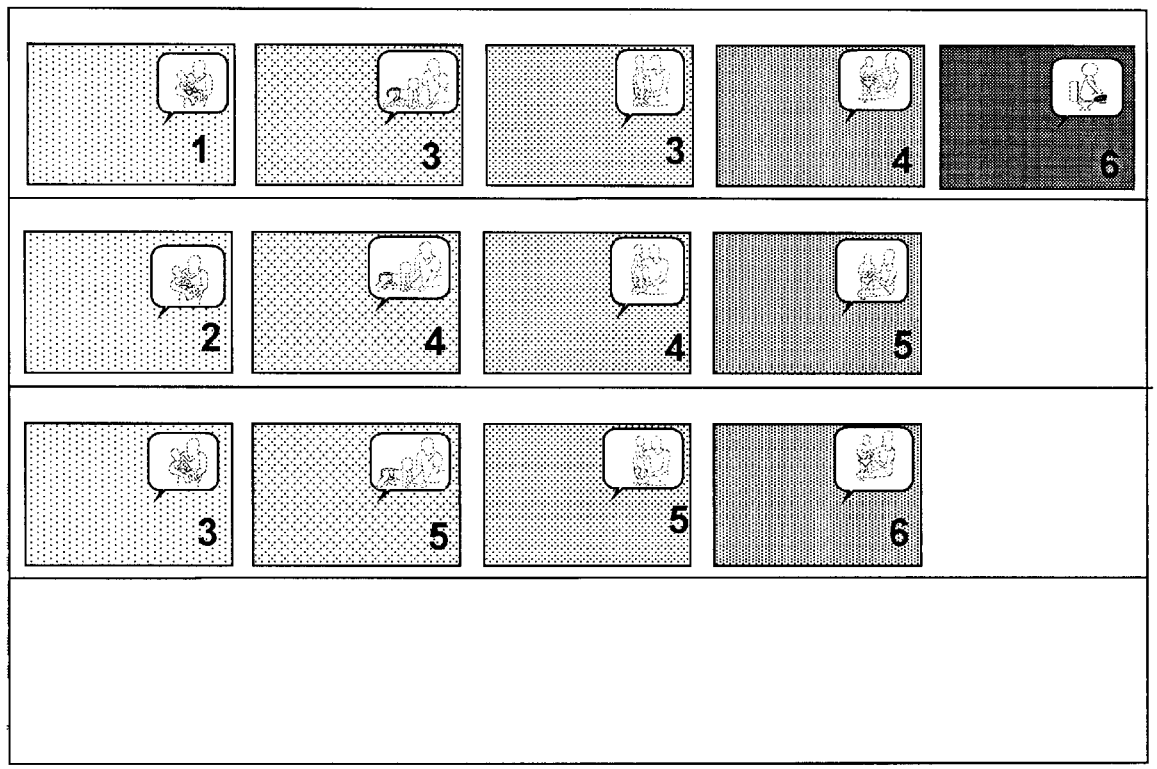
FIGURE: 3a

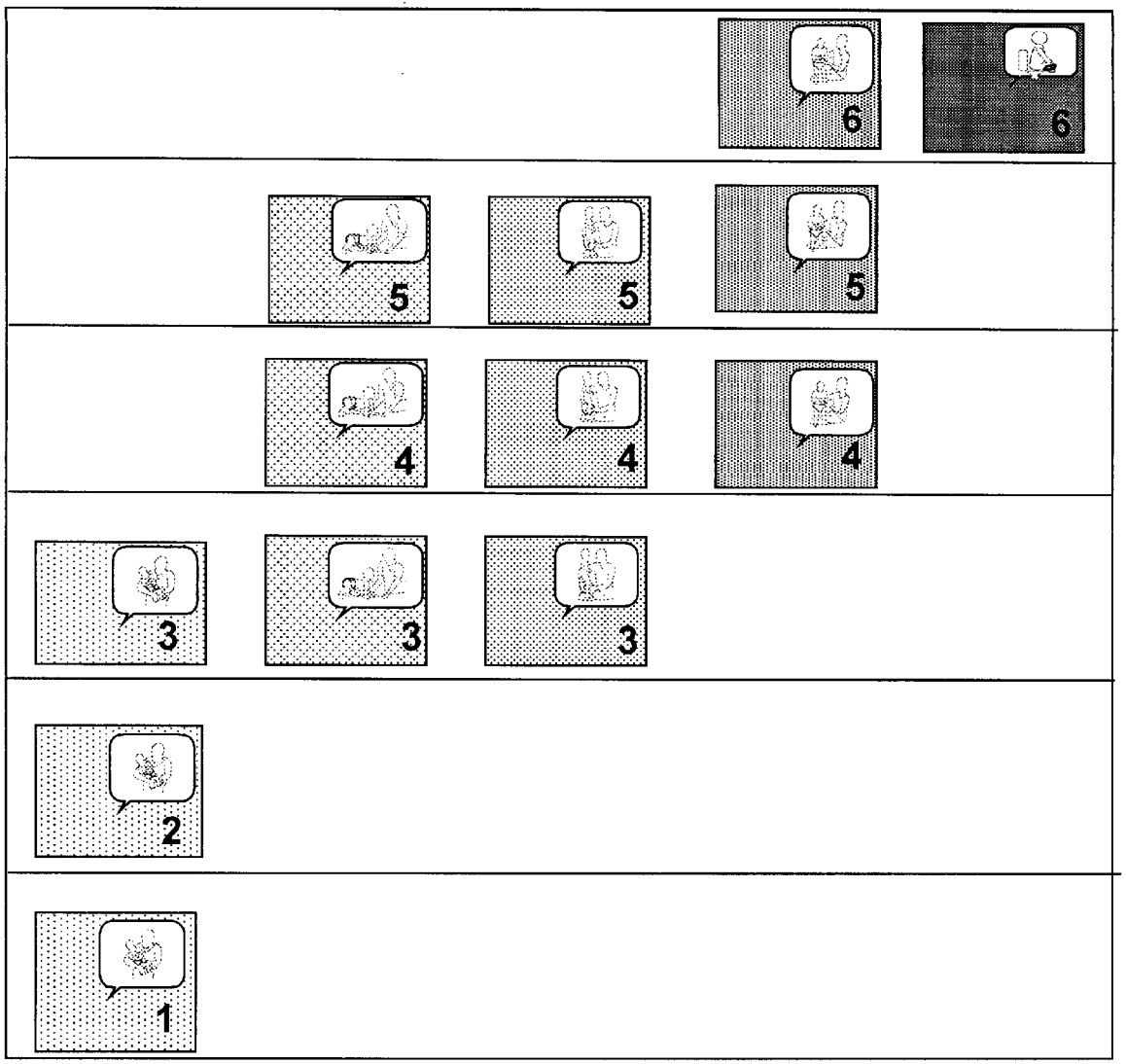
FIGURE: 3b

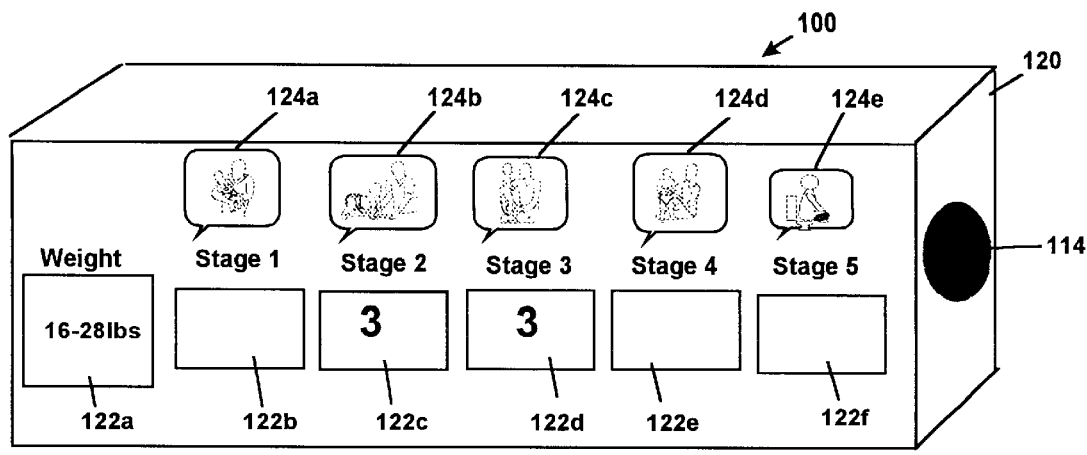
Figure: 4a
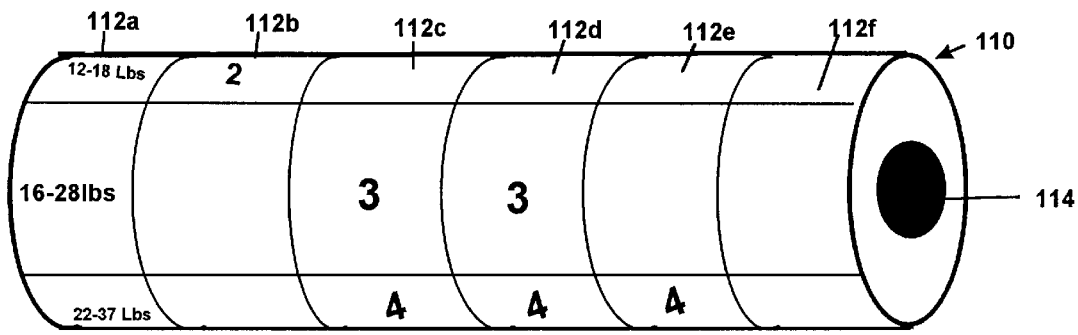
Figure: 4b
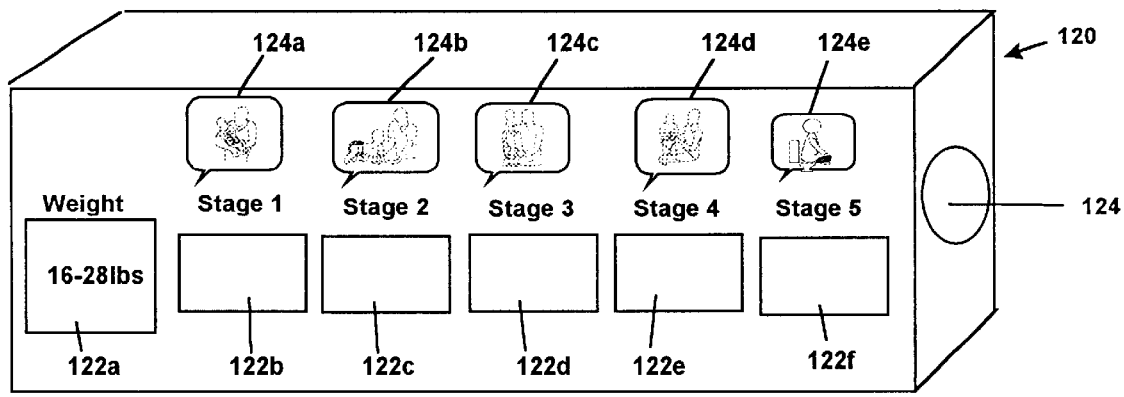
Figure: 4c

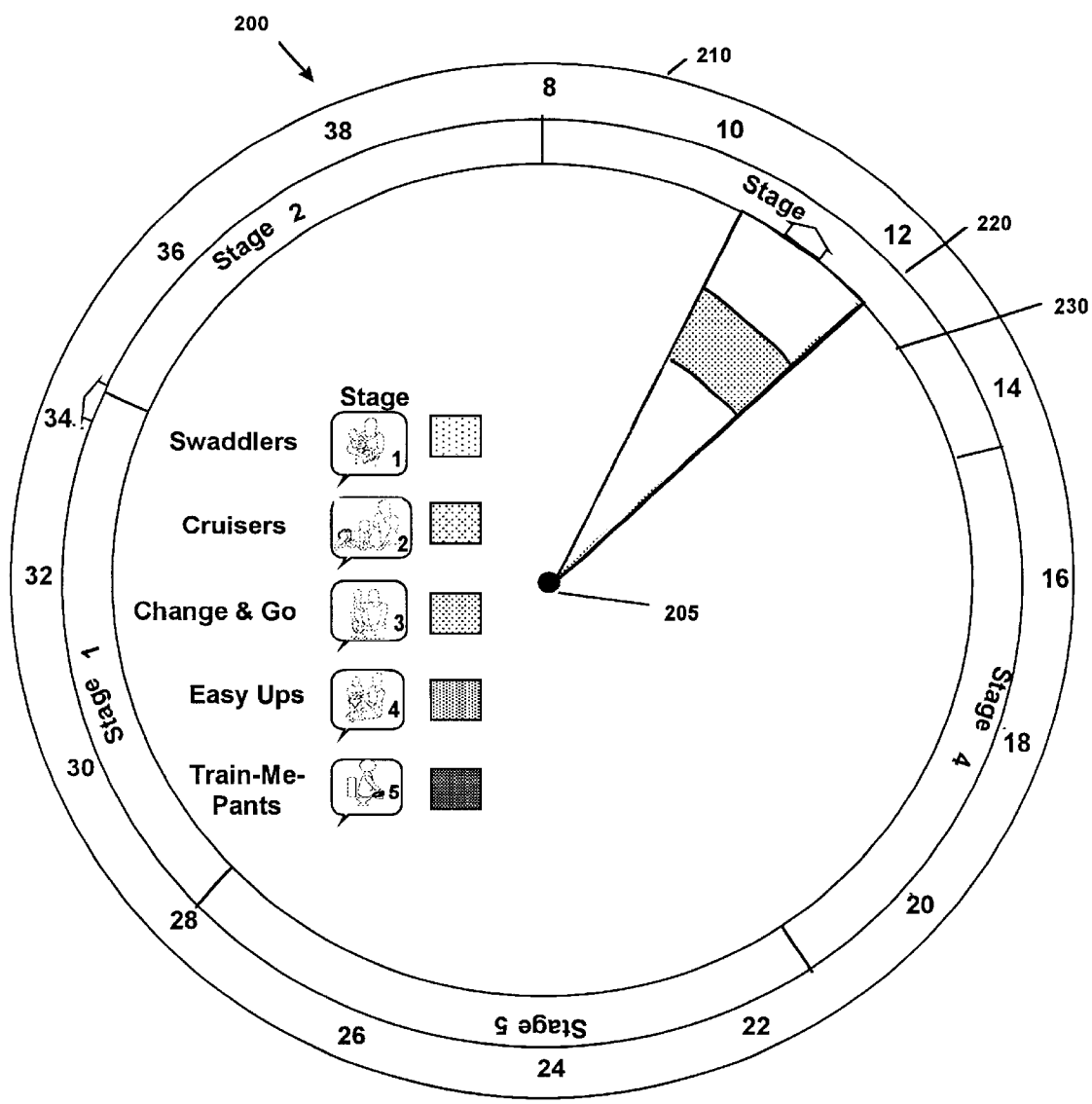
FIGURE: 5a

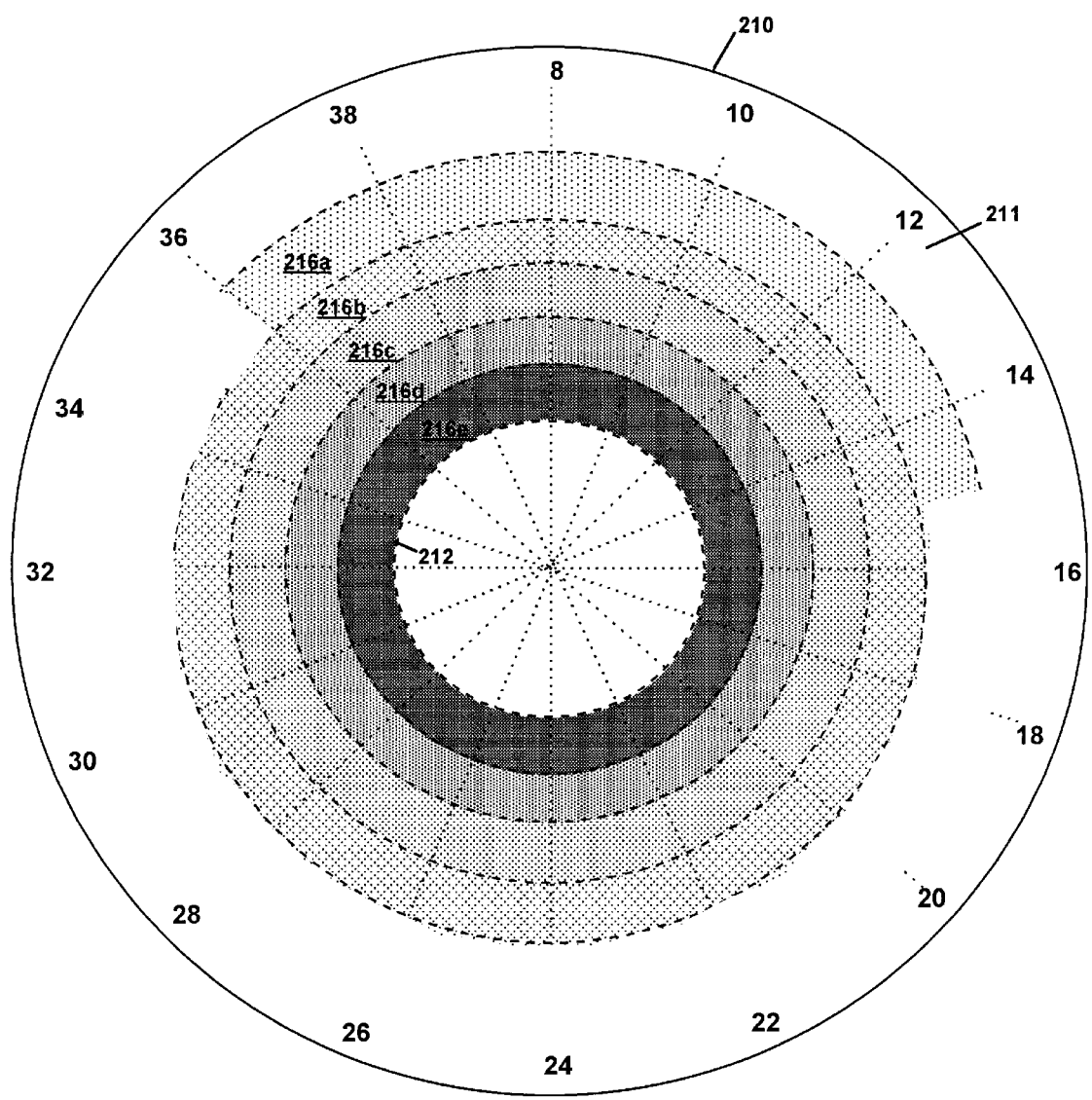
FIGURE: 5b

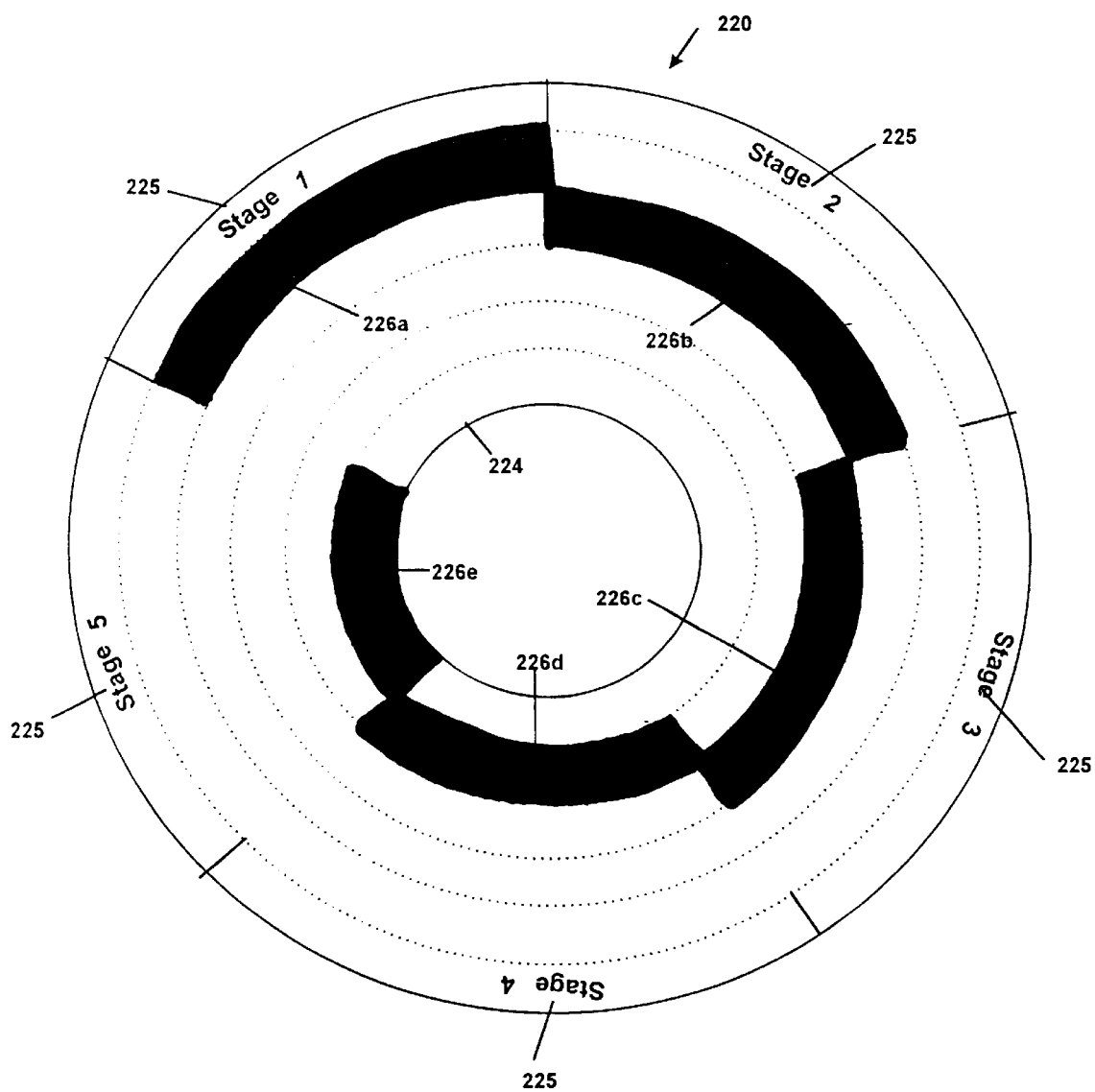
FIGURE: 5c

ARRAY OF DISPOSABLE ABSORBENT ARTICLE CONFIGURATIONS AND MERCHANDISE DISPLAY SYSTEM FOR IDENTIFYING DISPOSABLE ABSORBENT ARTICLE CONFIGURATIONS FOR WEARERS

FIELD OF THE INVENTION

The present invention is directed to an array of disposable absorbent article configurations and a system and device for identifying a disposable absorbent article configuration for a particular wearer.

BACKGROUND OF THE INVENTION

Disposable absorbent articles such as diapers and catamenials are designed to absorb and contain bodily waste to prevent soiling of the body and clothing. The disposable absorbent articles typically comprise a single design available in different sizes to fit a variety of wearers ranging from newborns to active toddlers. The design of the diaper typically affects performance, such as, ability to absorb and contain bodily waste. The size of the diaper typically affects fit, for example, the size of the diaper waist opening, the size of the openings around the thighs, and the length or "pitch" of the diaper.

The problem with a one design fits all approach is that a single configuration may not be appropriate for every level of activity and capability. For instance, caregivers for newborns and immobile infants may desire a soft, yet bulky design which wraps the wearer and is gentle on the wearer's skin whereas once the infant becomes actively mobile it may be more desirable to have a contoured trim fit design providing the wearer more freedom of movement. Other designs may also be desired as the toddler grows and becomes more and more capable of independent activity. For instance, a pull on diaper design may be beneficial for toddlers participating in the dressing experience. Similarly, a training diaper design may be appealing to a toddler in the toilet training stage which makes a wearer aware when a discharge of bodily waste has occurred while at the same time provide the necessary protection to the wearer's clothing. It is difficult to design a single product configuration exhibiting each of these attributes. Thus, there is need for a variety of disposable diaper designs matching a particular wearer's capability and/or level of activity.

Although providing a variety of diaper designs matching an infant or toddlers capability and/or level of activity may meet a consumer need, physical sizes of infants and toddlers vary throughout their development. As a result, different product designs are preferably made available in the same sizes. For instance, a disposable diaper designed for a crawling toddler may be available in the same size as a configuration designed for a walking toddler and/or a configuration designed for a toddler participating in the dressing experience. Merchandising systems typically display and arrange disposable diapers according to size numbers. Therefore, an unprecedented introduction of such a variety of disposable diaper configurations may present a consumer with a dilemma in choosing the right configuration for a particular wearer. Thus, there is also a need for a merchandising system which can enable a caregiver to select a design from a variety of configurations that matches a particular wearer's needs. Particularly, there is a need for a merchandising system that enables the caregiver to identify an absorbent article configuration designed for a particular wearer's stage of development.

SUMMARY OF THE INVENTION

In accordance with one aspect of the present invention, an array of disposable absorbent article configurations is provided comprising a sequence of designs corresponding to a wearer's stages of development. For a disposable diaper, the array of disposable absorbent article configurations may comprise a first absorbent article configuration having a chassis designed for newborns and immobile infants, a second absorbent article configuration having a chassis designed for mobile toddlers in a crawling stage, a third absorbent article configuration having a chassis designed for walking toddlers and other absorbent article configurations discussed further hereinafter in the detailed description of the invention.

The present invention is also directed to a merchandising system that facilitates a consumer's selection of an absorbent article configuration by appropriately matching a configuration of absorbent article with a particular wearer's stage of development. The system includes indicia exhibiting pictorial representations of the absorbent article configurations fitted to wearer's at corresponding stages of development. By looking at the indicia, a consumer can select the appropriate absorbent article configuration matching their particular wearer. The indicia may be provided on a display panel above the store shelves on which the absorbent article configurations are displayed for sale. The indicia may also be disposed on packaging for the absorbent article configurations.

The present invention also provides a device for selecting an absorbent article configuration by matching a particular configuration with a wearer's stage of development. The device may comprise a stationary component and a moveable component. The stationary component has a first wearer characteristic disposed thereon where the first wearer characteristic includes at least two first wearer characteristic types. The moveable component has a second wearer characteristic disposed thereon where the second wearer characteristic includes at least two second wearer characteristic types. The first wearer characteristic may include a wearer's weight and the second wearer's characteristic may include a wearer's stage of development. A consumer may select the appropriate absorbent article configuration for a wearer by moving the moveable component relative to the stationary component in order to match the wearer characteristics on the two components for a particular wearer.

The foregoing systems and devices can be employed relative to disposable diapers and other absorbent articles having a range of sizes and a variety of designs.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

FIG. 1 illustrates indicia exhibiting pictorial representations of absorbent article configurations fitted to wearer's at corresponding stages of development.

FIG. 2a illustrates a store display of absorbent article configurations having chassis designed to match a wearer's stage of development comprising a vertical arrangement where each shelf carries a different stage of development.

FIG. 2b illustrates the arrangement shown in FIG. 2a with absorbent article configurations arranged in a second order in columns according to size.

FIG. 3a illustrates a store display of absorbent article configurations having chassis designed to match a wearer's stage of development comprising a horizontal arrangement where the different stages of development are arranged in columns.

FIG. 3b illustrates the arrangement shown in FIG. 3a with absorbent article configurations arranged in a second order in rows according to size.

FIG. 4a illustrates a rotary cylinder type selection device used to facilitate a consumer's selection of the appropriate absorbent article configuration matching a particular wearer's stage of development.

FIG. 4b illustrates the rotary cylinder portion of the rotary cylinder type selection device illustrated in FIG. 4a.

FIG. 4c illustrates the housing portion of the rotary cylinder type selection device illustrated in FIG. 4a.

FIG. 5a illustrates an interactive dial type selection device according to the present invention used to facilitate a consumer's selection of the appropriate absorbent article configuration matching a particular wearer's stage of development.

FIG. 5b illustrates the base wheel portion of the dial type selection device illustrated in FIG. 5a.

FIG. 5c illustrates the middle wheel portion of the dial type selection device illustrated in FIG. 5a.

DETAILED DESCRIPTION OF THE INVENTION

The present invention is directed to an array of disposable absorbent article configurations comprising a sequence of designs corresponding to a wearer's stages of development and a merchandising system for identifying the configuration of absorbent article which matches a wearer's stage of development. For instance, the array may include a first absorbent article configuration designed for newborns and immobile infants, a second absorbent article configuration designed for a toddler in the crawling stage, and/or other absorbent article configurations designed for subsequent stages of development discussed below. The merchandising system generally includes indicia exhibiting pictorial representations of the absorbent article configurations fitted to wearers at respective stages of development enabling a consumer to identify the appropriate configuration that matches a particular wearer's stage of development. The system is particularly useful for merchandising multiple absorbent article configurations that are available in overlapping size ranges.

As used herein, the term "absorbent article" refers to devices which are designed to absorb and contain bodily exudates, and, more specifically, refers to devices which are placed within, against, or in proximity to, the body of the wearer to absorb and contain the various exudates discharged from the body. As used herein the term "chassis" refers to the main structure of the diaper. As used herein, the term "stage of development" refers to level of emotional and cognitive maturity and/or the physical abilities of an individual including locomotion, mobility, motor skills and coordination. As used herein the term "diaper" refers to an absorbent article generally used by infants and incontinent persons that is worn about the lower torso of the wearer. As used herein the term "chassis" refers to the main structure of the diaper with other features added to form the composite diaper structure. The term "disposable" is used herein to describe absorbent articles which are generally not intended to be laundered or otherwise restored or reused as an absorbent article (in other words, they are generally intended to be discarded after a single use, and, preferably, to be disposed of in an environmentally compatible manner). References to identifying a "size" is used herein to include a direct or indirect identification of a disposable diaper or other absorbent article size, such as by number or letter (for example, "Size 3" or "Size A"), by direct description (for example, "Small" or "Large"), or by any combination thereof, and whether expressed or discernible visually, audibly or otherwise. As used herein, "indicia" is an identifying marking, which may include words and/or graphics describing a product in use.

The array of absorbent articles and merchandising system described herein may be applicable to a number of absorbent article products. For instance, feminine hygiene garments may be made available in a variety of designs depending on a wearer's level of activity. However, a preferred embodiment includes an assortment of disposable diapers made available in a variety product configurations where each configuration includes distinguishable characteristics comprising structural differences addressing a wearer's stage of development. The stages of development may range from newborns to active toddlers seeking independence. For instance, a first stage of development might cover a prelocomotive phase and include newborns in a bonding stage with mom and other immobile infants whose level of activity might include a little more than head raising or rolling over. A second stage of development might cover a discovering stage comprising a crawling phase and include curious toddlers developing activity in the form of sitting and mobility in the form of scooting, rolling and crawling. A third stage of development might cover an exploring stage comprising a walking phase and include toddlers whose level of activity includes standing, walking and beginning to run. A fourth stage of development might cover a learning phase and include toddlers capable of doing things by themselves such as dressing and developing coordination which enables them to walk and run without losing balance. A fifth stage of development might cover a training stage and include toddlers undergoing toilet training, attempting to achieve independence and overall, undergoing a transition from baby to child. Other stages are contemplated.

For each or any of the aforementioned stages of development, a separate absorbent article configuration may be provided. For example, for the first stage of development, the absorbent article configuration may comprise a chassis designed to swaddle the wearer like a blanket and include a blanket like feel. This configuration might also include special structural features like an umbilical chord notch and also ornamental features such as graphics which include pastel colors and back to sleep logos. For the second stage of development, a second absorbent article configuration may comprise a chassis designed to gently conform to the wearer in order to enable more freedom of movement. For this second configuration, the chassis might be contoured having a relatively narrow crotch region, a stretchable high back region and a low cut front region and also include bright color graphics. The third absorbent article configuration may comprise a chassis having flexible fasteners and high stretch sides to facilitate easy, struggle-free changes of a toddler in a standing or lying position. The fourth absorbent article configuration may comprise a pull on chassis designed to look more like underwear that a wearer can put on and off enabling him or her to participate in the dressing experience. For the fifth stage of development, the fifth absorbent article configuration may comprise a chassis providing the comfort of underpants and the protection of a diaper while at the same time include a wetness indicator that enables the wearer to recognize the discomfort associated with wetting.

Since infants and toddlers experience stages of development at different rates, multiple sizes may be provided for each absorbent article configuration. As a result, different absorbent article configurations are made available in overlapping size ranges. For instance, the first absorbent article configuration might be available in a size one, a size two and a size three, while the second absorbent article configuration might be available in a size three, a size four and a size five. The third absorbent article configuration might be available in a size three, a size four and a size five while the fourth absorbent article might be available in a size four, a size five and a size six, and so on.

Overlapping size ranges make it difficult for a consumer to choose the right product configuration matching a particular wearer's stage of development. For this reason, a merchandising system is provided that facilitates consumers' selection of an absorbent article from a variety of configurations. The system preferably includes indicia exhibiting pictorial representations of the absorbent article configurations fitted to wearers at corresponding stages of development. As shown in FIG. 1, the indicia for the first absorbent article configuration 10 might display an infant cradled in a mother's arms. Similarly, the indicia for the second absorbent article configuration 12 might exhibit a toddler crawling while the indicia for the third configuration 14 might exhibit a mother changing the absorbent article while the wearer is standing. The indicia for the fourth absorbent article configuration 16 might show a wearer pulling the absorbent article up like underpants as the wearer participates in the dressing experience. Further, the indicia for the fifth absorbent article configuration 18 might show a toddler undergoing toilet training.

By matching the stage of development of a wearer with the stage of development exhibited by the indicia, the consumer can choose the right product configuration for their particular wearer. The indicia may be provided on a display panel disposed above the store shelves on which the absorbent article configurations are displayed for sale. Alternately, the indicia may be disposed on packaging for the different absorbent article configurations or in advertisements disseminated to the public.

The merchandising system may also include different product names associating each product configuration with the particular stage of development for which the product is designed. For instance, the first absorbent article configuration could be named Swaddlers 20, while the second, third, fourth, and fifth product configurations could be named Cruisers 22, Change & Go 24, Easy Ups 26 and Train-Me Pants 28, respectively. Each of the product names listed are trade names of products manufactured by The Procter and Gamble Company.

In addition to providing indicia displaying the absorbent article configurations in use and the different product names, the variety of absorbent article configurations may be displayed on store shelves in an arrangement that facilitates the consumer's selection. For instance, the absorbent article configurations may be arranged in a first sequential order according to the stages of development and in a second sequential order according to size. For this arrangement, the first article displayed is the first absorbent article configuration, consecutively followed in the first direction by the second, third, fourth and fifth absorbent article configurations. The first, second, third, fourth and fifth configurations are then arranged according to their available sizes in a second sequential order. For example, as shown in FIG. 2a, the first sequential order may be vertical with the first configuration displayed on a lowest shelf of the display and the fifth configuration displayed above on the highest shelf of the display, or vice versa. For this arrangement, sizes for each of the absorbent article configurations are arranged horizontally in the second sequential order with increasing sizes progressing from left to right. In an alternate embodiment shown in FIG. 2b the sizes are arranged in columnar form to further facilitate the consumer's selection process. Optionally, as shown in FIG. 3a, the first sequential order may be horizontal across a given shelf with first, second, third, fourth and fifth configurations displayed, progressing from left to right, on a given shelf. For this arrangement, the sizes for each absorbent article configuration are arranged vertically in the second sequential order with each shelf carrying a different size. In an alternate embodiment shown in FIG. 3b the sizes are arranged such that each shelf in the display carries a different size in order to better distinguish the different product configurations. Although the arrangements shown FIGS. 3a and 3b depict the sizes progressing upward, a reverse arrangement with the sizes increasing downward is contemplated.

Selection devices may be deployed in stores to help consumers to choose the right product configuration for their particular wearers. For example, a selection device may comprise a mechanical device for identifying an absorbent article configuration by matching a particular configuration with a wearer's stage of development. Such device may comprise a stationary component and a moveable component. The stationary component has a first wearer characteristic disposed thereon where the first wearer characteristic includes at least two first wearer characteristic types. The moveable component has a second wearer characteristic disposed thereon where the second wearer characteristic includes at least two second wearer characteristic types. The first wearer characteristic may include a wearer's weight and the second wearer's characteristic may include a wearer's stage of development. A consumer may select the appropriate absorbent article configuration for a wearer by moving the moveable component relative to the stationary component in order to match the characteristics on the device with the characteristics of a particular wearer.

Examples of mechanical type selection devices include slides, rotary dials and rotary cylinders. A rotary cylinder type selection device 100 is illustrated in FIG. 4a. As shown, the device includes a cylinder 110 enclosed and rotatably supported in a housing 120. The cylinder 110, shown in FIG. 4b, is divided into segments along a length and includes a series of weight ranges disposed circumferentially around the cylinder in a first segment 112a and available sizes for each absorbent article configuration disposed circumferentially around the cylinder in succeeding segments 112a–112f. For each weight range provided in the first segment 112a of the cylinder 110, a corresponding size number, if available for a given absorbent article configuration, is disposed in alignment therewith in the succeeding segments. The cylinder 110 also includes a knob 114 for rotating the cylinder 110. The housing 120, shown in FIG. 4c, is also divided into segments along a length corresponding to the cylinder segments. Each of the housing segments includes a window 122a–122f exposing the cylinder segments and indicia 124a–124e disposed above the windows exhibiting the product configuration corresponding to a wearer's stages of development. The housing 120 may also includes a slot 124 exposing the cylinder knob 114. In operation, the consumer rotates the knob 114 to the weight range matching their particular wearer. For given weight range, an available size, if any, appears in the windows 124a–124f in each segment of the housing. From the indicia disposed above the windows 124a–124f, the consumer can select the correct size and the appropriate product configuration for their particular wearer.

Other mechanical devices such as a dial could be employed which permits a person to actively "dial in" information regarding the characteristics of the potential wearer of interest, and which would then identify or allow the person to identify a size and absorbent article configuration which is fit-appropriate for that wearer. FIG. 5a illustrates an example of an interactive mechanical dial-type selection device for disposable diapers which embodies the present invention. The dial type selection device 200 comprises a base wheel 210, a middle wheel 220, and a top wheel 230. The wheels are held together by an axle 205, the axle 205 preferably having a broadened portion or cap at each end to keep the wheels from slipping off the axle. Both the middle 220 wheel and the top wheel 230 can be rotated around the axle 205 relative to the base wheel 210 and relative to each other. As shown in FIG. 5b, the base wheel 210 has a radially outward portion 211 labeled with weight values around the circumference of radially outboard portion 211. As shown in FIG. 5b, the base wheel 210 also has a radially inward portion 212 labeled with a spiral of a series of different colored (or otherwise differentiated) segments 216a–216e. The different colors correspond to the different diaper configurations which are discussed hereinafter in connection with FIG. 5a. FIG. 5c shows middle wheel 220 having a radially outward portion 222 labeled with stages of development 225 and a radially inward portion 224 with a spiral of cutout segments or openings 226a–226e designed to overly a portion of the different color segments on the base wheel 210. Middle wheel 220 also has a pointer 228. As shown in FIG. 5a, top wheel 230 is labeled with a diaper configuration key 232 having five segments 234a–234e, where each segment corresponds to a different absorbent article configuration. Each such segment 234a–234e in the diaper configuration key 232 has a different color, and each color corresponds to a respective color of different-colored segments 216a–216e on base wheel 210. Top wheel 230 also has a pointer 236, and a wedge-shaped cutout or opening 238 designed to overlie cutout segments 226a–226e in the middle wheel 220. Other configurations providing the same or similar information are possible.

Referring again to FIG. 5a, a user such as a consumer or other caregiver can "dial in" a value for a potential wearer's weight by rotating middle wheel 220 to move pointer 228 to point to the appropriate weight value on base wheel 210. The user can also "dial in" a value for the potential wearer's stage of development by rotating top wheel 230 to move pointer 236 to point to the appropriate stage of development 225 on middle wheel 220. Once the combination of a wearer stage of development and a wearer weight value is dialed in, one of the segments 216a–216e from the base wheel 210 will be visible through the cut-out segments or openings 226 in middle wheel 220 as well as through the wedge-shaped cutout or opening 238 in top wheel 230 (in the example illustrated in FIG. 5a, the visible segment corresponds to a colored segment 216c). The user can then associate or match the color of the visible one of colored segments 216a–216e to one of the colors 234a–234e on diaper configuration key 232 which thereby identifies the configuration and size predicted to be appropriate for the wearer having the combined weight and stage of development dialed-in by the user (in the example illustrated in FIG. 5a, diaper configuration, Cruisers). As will be apparent to a person skilled in the art from the disclosure of this embodiment of the invention, other mechanical devices such as a slide rule type device could be used in place of the dial to identify an appropriate diaper configuration or other absorbent article configuration a similar fashion.

Interactive devices including one or more computers, hand held devices, scanners, etc. can also be utilized as selection devices for disposable absorbent articles where multiple configurations are involved. Such devices could prompt a person such as a consumer or caregiver to actively input answers to questions regarding the pertinent characteristics of the potential wearer of interest, keep track of the answers, and provide output information identifying or allowing the person to identify a disposable diaper configuration or other article appropriate for that wearer based on those answers. Such an "actively interactive" device could be employed as part of an interactive in-store display, as part of an interactive site on the World Wide Web, or as part of an interactive menu-driven phone system. Configuration identification information could be provided or output visually in the form of a figure, symbol or other indicia identifying a particular configuration, or could be provided or output audibly such as through a message from an interactive phone system.

It should be understood that while particular embodiments and/or features of the invention have been described, it would be apparent to those skilled in the art (given the present description) that various other changes and modifications can be made without departing from the spirit and scope of the invention. Further, it should be apparent that all combinations of such embodiments and/or features are possible and can result in preferred executions of the invention. It is therefore intended to cover in the appended claims all such changes and modifications that are within the spirit and scope of the invention.

What is claimed is:

1. An army of disposable diaper configurations designed to fit wearers at different stages of development, the array comprising:

a first disposable diaper configuration, the first disposable diaper configuration including a chassis designed with specific features to correspond to a wearer's first stage of development, wherein the wearer's first stage of development comprises a pre-locomotive phase wherein the wearers include newborn infants and immobile toddlers and wherein the specific features include blanket like feel and an umbilical notch;

a second disposable diaper configuration, the second disposable diaper configuration including a chassis designed with specific features to correspond to a wearer's second stage of development; and a third disposable diaper configuration, the third disposable diaper configuration including a chassis designed with specific features to correspond to a wearer's third stage of development.

2. An may of disposable diaper configurations designed to fit wearers at different stages of development, the array comprising:

a first disposable diaper configuration, the first disposable diaper configuration including a chassis designed with specific features to correspond to a wearer's first stage of development;

a second disposable diaper configuration, the second disposable diaper configuration including a chassis designed with specific features to correspond to a wearer's second stage of development, wherein the wearer's second stage of development comprises a crawling phase wherein the wearers are capable of scooting, rolling, and crawling and wherein the specific features include a contoured shape comprising a narrow crotch, a stretchable high back region, and a low cut front region; and a third disposable diaper configuration, the third disposable diaper configuration including a chassis designed with specific features to correspond to a wearer's third stage of development.

3. An array of disposable diaper configurations designed to fit wearers at different stages of development, the array comprising:

a first disposable diaper configuration, the first disposable diaper configuration including a chassis designed with specific features to correspond to a wearer's first stage of development, wherein the wearer's first stage of development comprises a pre-locomotive phase wherein the wearers include newborn infants and immobile toddlers and wherein the specific features include blanket like feel and an umbilical notch;

a second disposable diaper configuration, the second disposable diaper configuration including a chassis designed with specific features to correspond to a wearer's second stage of development; and a third disposable diaper configuration, the third disposable diaper configuration including a chassis designed with specific features to correspond to a wearer's third stage of development, wherein the wearer's third stage of development comprises a walking phase wherein the wearers are capable of standing, walking and beginning to run and wherein the specific features include flexible fasteners and high stretch sides.

4. An array of disposable diaper configurations designed to fit wearers at different stages of development, the array comprising:

a first disposable diaper configuration, the first disposable diaper configuration including a chassis designed with specific features to correspond to a wearer's first stage of development;

a second disposable diaper configuration, the second disposable diaper configuration including a chassis designed with specific features to correspond to a wearer's second stage of development;

a third disposable diaper configuration, the third disposable diaper configuration including a chassis designed with specific features to correspond to a wearer's third stage of development, and a fourth disposable diaper configuration, the fourth disposable diaper configuration including a chassis designed with specific features to correspond to a wearer's fourth stage of development, wherein the fourth stage of development comprises a learning phase wherein the wearers are capable of participating in a dressing experience and wherein the specific features include a pull on chassis designed to look like underwear; and a fifth disposable diaper, the fifth disposable diaper configuration including a chassis designed with specific features to correspond to a wearer's fifth stage of development, wherein the fifth stage of development comprises a training phase wherein the wearers are undergoing toilet training and wherein the specific features include a wetness indicator that enables the wearer to recognize the discomfort associated with wetting.

* * * * *

UNITED STATES PATENT AND TRADEMARK OFFICE
CERTIFICATE OF CORRECTION

PATENT NO.     : 6,648,864 B2
DATED           : November 18, 2003
INVENTOR(S)  : Karl P. Ronn et al.

It is certified that error appears in the above-identified patent and that said Letters Patent is hereby corrected as shown below:

Column 4,
Line 24, delete "prelocomotive" and insert -- pre-locomotive --.

Column 8,
Line 39, delete "army" and insert -- array --.
Line 58, delete "may" and insert -- array --.

Signed and Sealed this

Twenty-second Day of June, 2004

JON W. DUDAS
*Acting Director of the United States Patent and Trademark Office*